US012784869B2

(12) United States Patent
Folch Fortuny

(10) Patent No.: US 12,784,869 B2
(45) Date of Patent: Nov. 3, 2026

(54) METHOD AND SYSTEM FOR PREDICTION OF A PERFORMANCE OF A STRAIN IN A PLANT

(71) Applicant: DSM IP ASSETS B.V., Heerlen (NL)

(72) Inventor: Abel Folch Fortuny, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 475 days.

(21) Appl. No.: 17/780,258

(22) PCT Filed: Dec. 17, 2020

(86) PCT No.: PCT/EP2020/086672

§ 371 (c)(1),
(2) Date: May 26, 2022

(87) PCT Pub. No.: WO2021/122917

PCT Pub. Date: Jun. 24, 2021

(65) Prior Publication Data

US 2022/0415431 A1 Dec. 29, 2022

(30) Foreign Application Priority Data

Dec. 19, 2019 (EP) .................................... 19218043

(51) Int. Cl.
*G16B 5/00* (2019.01)
*G16B 40/20* (2019.01)

(52) U.S. Cl.
CPC ............... *G16B 5/00* (2019.02); *G16B 40/20* (2019.02)

(58) Field of Classification Search
None
See application file for complete search history.

(56) References Cited

U.S. PATENT DOCUMENTS 6,966,374 B2 * 11/2005 Vinegar ................ E21B 43/305 166/272.3
2004/0002108 A1 * 1/2004 Hilser .................... G16B 15/20 435/7.1

(Continued)

FOREIGN PATENT DOCUMENTS

CN 101370926 A 2/2009
RU 2553550 C2 * 6/2015 ............. C11D 3/386

OTHER PUBLICATIONS

Biomass estimation in batch biotechnological processes by Bayesian Gaussian process regression, Fernando di Sciascio, 2008 (Year: 2008).*

(Continued)

*Primary Examiner* — Shelby A Turner
*Assistant Examiner* — Brandon J Becker
(74) *Attorney, Agent, or Firm* — McBee, Moore & Vanik IP, LLC

(57) ABSTRACT

A method and system for predicting performance of strains in processes, the strains being capable of fermentation of biomass for production of at least bio-ethanol, the method including the steps of: receiving a first process data set related to a performance of a first strain in a first process for producing bio-ethanol at a first site, receiving a second process data set related to a performance of a second strain in the first process for producing bio-ethanol at the first site, receiving a third process data set related to a performance of the first strain in a second process for producing bio-ethanol at a second site, the second site being different from the first site, and wherein the first, second and third process data sets each include one or more process profiles and/or process responses, determining a first correlation between the first process data set and the second process data set, and determining a second correlation between the first process data and the third process data, and reconstructing a fourth (Continued)

process data set related to a performance of the second strain in the second process for producing bio-ethanol at the second site by missing data imputation, wherein the fourth process data set is estimated based on the first correlation and the second correlation.

18 Claims, 5 Drawing Sheets

(56) References Cited

U.S. PATENT DOCUMENTS

| | | | | |
|---|---|---|---|---|
| 2008/0109200 | A1* | 5/2008 | Bartee | C12P 7/06 703/12 |
| 2009/0326695 | A1 | 12/2009 | Macharia | |
| 2010/0093046 | A1* | 4/2010 | Remmereit | C02F 3/34 435/162 |
| 2011/0033854 | A1* | 2/2011 | Drmanac | C40B 40/06 435/6.12 |
| 2013/0130334 | A1* | 5/2013 | Reguera | C12P 7/14 435/162 |
| 2014/0136146 | A1 | 5/2014 | Mccready | |
| 2016/0237442 | A1* | 8/2016 | Puri | C12N 1/205 |
| 2018/0016592 | A1* | 1/2018 | Chen | C12N 9/0061 |
| 2018/0216101 | A1* | 8/2018 | Serber | C12N 15/1058 |

OTHER PUBLICATIONS

International Search Report received in international application No. PCT/EP2020/086672, mailed Feb. 12, 2021.

Imtiaz et al., "Treatment of missing values in process data analysis," Canadian Journal of Chemical Engineering, vol. 36, No. 5, Sep. 27, 2008, pp. 838-858.

Di Sciascio et al., "Biomass estimation in batch biotechnical processes by Bayesian Gaussian process regression," Computers & Chemical Engineering, Pergamon Press, Oxford, GB, vol. 32, No. 12, Dec. 22, 2008, pp. 3264-3273.

* cited by examiner

METHOD AND SYSTEM FOR PREDICTION OF A PERFORMANCE OF A STRAIN IN A PLANT

CROSS-REFERENCE TO RELATED APPLICATIONS

This application is the National Stage entry of International Application No. PCT/EP2020/086672, filed 17 Dec. 2020, which claims priority to European Patent Application No. 19218043.8, filed 19 Dec. 2019.

BACKGROUND

Field

The invention relates to a method, system and computer program for predicting a performance of a strain in a bio-ethanol producing process, by fermentation of biomass.

Renewable energy is becoming increasingly more important, with limited energy sources, such as fossil fuels getting replenished. Additionally, increasing levels of greenhouse pollution resulting from the combustion of fossil fuels are attributing to global warming and other ecological disasters. Bio-fuels, such as bio-ethanol, could provide important advantages in future energy solutions.

Bio-ethanol constitutes a renewable fuel source that could be developed to be completely sustainable in the future. The net release of carbon dioxide is zero for burning of bio-ethanol, and its sulfur content is very low. Bio-ethanol has therefore a strongly reduced influence on greenhouse gases and the resulting influence on global warming, thus having far superior environmental properties than fossil fuels. Lastly, it should be feasible to make the production of bio-ethanol be economically favorable compared to mining fossil fuels. Multiple factors should be considered for this last argument; on the one side are fossil fuel sources becoming scarcer and thus more expensive to exploit, and on the other hand research is performed to make the production of bio-ethanol as efficient as possible.

Bio-ethanol is produced from a biomass source. Currently, much research is directed to developing the ideal feedstock for bio-ethanol production and how to optimize the bio-ethanol production process of said ideal feedstock. Multiple factors need to be taken into account: the chemical composition of the biomass, the cultivation practices, the availability of land and its land use practices, how the biomass resource is used and how much of the biomass can be used as bio-ethanol and/or other renewable resource, the total energy balance of the whole process, the balance of greenhouse gases, acidifying gases and ozone depletion gases, absorption of minerals to water and soil of the land mass the biomass is grown on, the presence or absence of pesticides, the possibility of soil erosion, whether the biomass production contributes to biodiversity, economical aspects, such as the farm-gate value of the biomass, logistic costs for the transportation and storage of biomass, the value of the co-products after production of bio-ethanol, employment opportunities, and lastly water requirements and availability of water.

Biomass comprises components that can roughly be divided in the following categories: cellulose, hemicellulose, lignin, extractives, ash and other compounds. Of these, cellulose, hemicellulose and lignin are the most abundant in biomass. Cellulose is a polysaccharide consisting of a linear chain of hundreds to thousands of β-[1→4]-linked D-glucose units. It is one the structural components of the primary cell wall of green plants, many algae and of oomycetes. Hemicellulose is a heteropolymer and a polysaccharide, and is easily hydrolyzed by either acid or base, or enzymatic. Examples of hemicelluloses include xylan, glucuronoxylan, glucomannan and xyloglucan. Lastly, lignin is a class of complex organic polymers and are cross-linked phenolic polymers. Lignins are important in the formation of cell walls and cause the biomass to be rigid. Usually, lignin is produced as a byproduct in the production of paper and is normally burned as fuel.

The biomass can be broken down into bio-ethanol by either chemical or enzymatic hydrolysis, or by microbial fermentation, such as is the case in beer brewing.

It can be challenging to predict whether microbial fermentation of biomass will be successful. Many factors play a role in this process, and it is not certain that a particular strain of microbes which performs well on one type of feedstock, will perform well on another type of feedstock. The metabolic process is in such cases often too complicated to understand or model, so, often, no predictions can be made based on these processes in an accurate way. In addition, experiments in lab environments do not always translate well to industrial-scale production plants, resulting in large losses and a huge setback in research.

There is a need to overcome these issues and/or avoid an expensive and time-consuming full test of a particular strain in a new plant.

SUMMARY

It is an object of the invention to provide for a method and a system that obviates at least one of the above-mentioned drawbacks.

Additionally or alternatively, it is an object of the invention to provide an improved prediction of a performance of a strain in a plant.

Thereto, the invention provides for a method for predicting performance of strains in processes, the strains being capable of fermentation of biomass for production of at least bio-ethanol. The method includes the steps of: receiving a first process data set related to a performance of a first strain in a first process for producing bio-ethanol at a first site, receiving a second process data set related to a performance of a second strain in the first process for producing bio-ethanol at the first site, receiving a third process data set related to a performance of the first strain in a second process for producing bio-ethanol at a second site, the second site being different from the first site, and wherein the first, second and third process data sets each include one or more process profiles and/or process responses, determining a first correlation between the first process data set and the second process data set, and determining a second correlation between the first process data and the third process data, and reconstructing a fourth process data set related to a performance of the second strain in the second process for producing bio-ethanol at the second site by missing data imputation, wherein the fourth process data set is estimated based on the first correlation and the second correlation.

The method thus allows for predicting a performance, instead of requiring trial-and-error. The trial-and-error method is highly expensive, requires long time, and the outcome is unpredictable. By providing a prediction of the outcome in a certain plant, less time may be required, and the outcome can become more predictable. Therefore, the costs involved can be greatly reduced.

The method according to the invention permits to exploit the specific relationships between data sets of strains at sites for imputing new unmeasured data sets. In this way, an improved predictive model can be built, suitable for the analysis of the performance of strains in new sites or plants. A certain number of strains may have been analyzed in a process at a first site, and a subgroup of these strains has also been characterized in the same process at a second site, different from the first site. This data can be used for determining relevant correlations needed for the missing data imputation of an untested strain at the second site.

Many parameters need to be considered in the fermentation of biomass into bio-ethanol. By comparing the performance of different strains of e.g. yeast in a certain plant, a prediction can be made when placed in a different plant, based on the performance of the other strain in this different plant.

In one example, the second strain is an improvement of the first strain, wherein the first strain is in use in the production of bio-ethanol from fermentation of biomass at a plant. By comparing the two strains in e.g. a laboratory environment, a prediction can be made on how well the improved strain will perform in the plant.

It will be appreciated that sites may be broadly interpreted as a location where a process is performed. In some examples, a site represents a plant, which can be an industrial production facility (cf. factory).

Various data types can be used for performing the prediction based on missing data imputation. The data may include process profiles, process responses and/or process conditions. Other additional process parameters/variables can also be taken into account. The process settings at the different plants may be different (e.g. one plant uses a larger quantity of an ingredient used in the process). End products, among others, bio-ethanol, are obtained by means of the processes using the strains. The processes may have the same steps, but the dimensions, parameters, etc. of the processes at the different sites may be different.

The process profiles may include time series data, for example values indicative of sugar, ethanol, other related compounds, temperature, pH profiles, etc., monitored during the process. Furthermore, setpoints or target values may be provided for the process. The process profiles may also include process responses, e.g. the amount of ethanol production is a key performance indicator of the process. It will be appreciated that various other responses of the process exist, for example glycerol levels, cell count, amount of yeast used in the process, etc.

Optionally, the reconstructed fourth process data set is used for fitting a predictive model configured to predict the performance of the second strain in the second process at the second site.

By means of missing data imputation, all the information contained in the available primary and secondary data sets can be exploited to entirely reconstruct the profiles associated with the strains that were not analyzed at the second site. These profiles can be optionally used for fitting an improved predictive model, suitable for the assessment of the performance of strains in new plants.

The predicted dataset can be modeled in order to get an even better prediction for the performance of the strain in the other plant. A predictive model is in this case ideal to achieve optimal prediction of the performance of the second strain in the second plant. In some examples, a predictive model can be configured to employ statistics for predicting outcomes.

Optionally, the predictive model is employed for adjusting operational parameters in order to improve the performance of the second strain in the second process at the second site.

The predictive model allows the input of process profiles and/or process responses. The predictive model can then give optimized process profiles for the predicted dataset, by optimizing the process responses. The model can thus predict the outcome of the model, depending on the input parameters.

Based on the prediction of the strain at the new site, changes can be performed on the process conditions and/or parameters in order to improve the performance (optimize), for example taking into account seasonable aspects. Advantageously, data obtained from different sites (e.g. ethanol plants) can be used for optimizing the process either in new sites or existing sites.

In some examples, additional 2D data with a recipe (cf. ingredients) used in the process at a site is added, temperatures, pH, etc. This information can also be added to the prediction model for the new plant. An optimization can be performed to set plant settings in order to improve one or more process profiles.

The missing data that is predicted can include the response. Based on that response, an optimization can be performed. It will be appreciated that different optimization algorithms can be used. For example, a plurality of predictions can be made (based on many process inputs), and it can be observed which input provides improved results. In some examples, a design of experiments optimization can be performed. A design of experiments response model may predict the optimized parameter set for the process.

When strain X is introduced in a new plant, it is possible that in some cases data is available for strain X for different plants. This information can also be used for optimizing the first plant. This information can then be fed back, possibly in combination with a prediction algorithm.

In some examples, a machine learning model (e.g. artificial intelligence model) can be employed for the prediction. A machine learning model can be configured to describe the relationship between input(s) and response(s).

Optionally, the first process at the first site is carried out in a laboratory, and wherein the second process at the second site is carried out in a plant, the plant preferably being an industrial-scale bio-ethanol production plant.

Already acquired data sets can be used for the prediction of missing data. However, advantageously, lab-experiments can also be used for obtaining newly data sets used for performing the prediction.

In some examples, data from two different strains in two different sites/plants may be required for obtaining the prediction. However, in some cases it may be challenging to have the data right for two different sites/plants, e.g. multiple conditions in industrial plants. In some examples, data available from one plant in which a trail of the strain is performed can be used. For example, the baseline in another plant may be available with only data relating to strain Y. According to the invention, it can be predicted what the results would be if strain X was used in a new plant, before having the process operational in the new plant. For instance, making the process operational in the new plant (cf. expensive procedure) may be skipped if the predictions are not satisfying. In some advantageous examples, the first site is a lab. It can be significantly easier to carry out small-scale lab-tests.

Optionally, one or more small-scale laboratory experiments are carried out in the laboratory for determining at least one of the first process data set or the second process data set.

Research for new strains may be preliminary performed in a laboratory environment, which is often desirable and advisable before experimenting on larger scale. By allowing to translate laboratory-scale experiments to a production plant, initial production costs can be greatly reduced.

In some examples, information relating to strain X in a plant 1 may not be available. For this, a small-scale test can be performed, for instance in a laboratory. Such a lab-scale test can be used to fill in information for being able to perform a prediction using the method according to the invention. For example, plant 1 can be lab-scale, e.g. performed in a laboratory or even a small test module. Advantageously, in this way, information from large-scale plants may not be needed for plant 1. It can be easier to perform lab-scale experiments, allowing more easy variations.

Optionally, the first process at the first site is modelled by means of a computational model, wherein the computational model is used for determining at least one of the first process data set or the second process data set.

A computational model may be utilized for modelling the process of bio-ethanol production. The computational model allows more flexibility in adjusting conditions and/or parameters in a process, hence enabling more design freedom. In some examples, the computational model has the advantage of having the possibility of being more accurate than non-computational models, because of the many parameters that can be taken into account.

Optionally, missing data related to the performance of the second strain in the second process at the second site is predicted at least in part using a regression model.

Regression analysis is a well-known method to simulate missing data. This can either comprise a linear and/or a nonlinear regression model, depending on the data sets.

Optionally, the regression model includes at least one of: multivariate regression, principal component regression, partial least squares regression, or trimmed scores regression for missing data imputation.

By implementing any of the above-mentioned regression models, a more accurate prediction can be made regarding the missing data of the fourth data set, comprising data related to the performance of the second strain in the second process at the second site.

Optionally, prior to determining the second correlation, data arrays in the data set relating to different batches in the first process data and the third process data are shuffled with respect to each other.

The data relating to batches may come from different sites (e.g. plants), e.g. for a first strain at a first site and the first strain at a second site. The strain may for instance be the only commonality in such a case. Hence, a batch of one site may not correspond to a batch of another site. Optionally, data can be shuffled in the data for the first strain at the first site and/or in the data for the first strain at the second site. The shuffle can generate sufficient variation to better capture the differences. In this way, the accuracy of the prediction may be improved.

Optionally, the data arrays are shuffled randomly or pseudo-randomly.

The rows can be permuted in different ways. For instance, the rows can be randomly or quasi-randomly permuted for the shuffle for obtaining better predictions.

Optionally, missing data related to the performance of the second strain in the second process at the second site is predicted at least in part using a trained artificial neural network model.

The artificial neural network may be trained using historic data. Artificial neural networks have the advantage of being easily moldable to the process at hand. It will be appreciated that other machine learning algorithms may also be employed.

Optionally, the first process at the first site and the second process at the second site are carried out in industrial-scale bio-ethanol production plants different from each other, preferably also at remote locations with respect to each other.

One of the main problems of bio-ethanol production of biological feedstock, is that between batches or sources of feedstock variety exists, for example due to a different climate or a different soil, different variant of said feedstock, etc. Therefore, we here provide a solution to predict how a change in any of the process parameters, will affect the output parameters, such as between two plants wherein different process parameters are required or necessary.

Optionally, the process data sets include for a plurality of time points a value indicative for at least one of a sugar consumption, ethanol production, pH value, reaction temperature, composition of biomass, enzyme composition, yeast cell count, or glycerol production, wherein preferably the process data sets further includes data relating to a plurality of batch processes.

Optionally, the processes at least partially involve the production of ethanol. In some examples, the process involves producing bio-ethanol using yeast strains. For example, a slurry of corn can be provided. This slurry can be guided to a propagation tank, in which the yeast is propagated. The produced product can then be guided to a fermentation tank. This can be followed by a distillation step. In some examples, a back-step is provided, e.g. product from the distillation (such as water) can be fed back to an earlier process step. In the process, the temperature may be controlled in one or more process steps. Therefore, one or more target temperature can be set. However, throughout the year there can be differences in temperatures outside, so the cooling unit(s) may not be able to adequately handle these outside temperature fluctuations. In general, the process can be predefined and/or preset. For instance, a same unit operation can be employed for a 'same' process. However, relatively small differences may exist in the conditions in which the process is carried out. For instance, some sites (e.g. plants) may have small variations in temperatures; the amount of (solid) bio-mass, e.g. corn, used in the process can be different; the pH-values can be different; the enzymes that are used for making the slurry can be different (e.g. different producers); the bio-mass itself, e.g. corn, can be different; seasonal influences (summer-winter); slightly different operational conditions; etc. These can result in small differences in a same predefined/preset process.

According to an aspect, the invention provides for a system for predicting performance of strains in processes, the system including means for carrying out a method for predicting performance of strains in processes, the strains being capable of fermentation of biomass for production of at least bio-ethanol. The method includes the steps of: receiving a first process data set related to a performance of a first strain in a first process for producing bio-ethanol at a first site, receiving a second process data set related to a performance of a second strain in the first process for producing bio-ethanol at the first site, receiving a third process data set related to a performance of the first strain in a second process for producing bio-ethanol at a second site, the second site being different from the first site, and wherein the first, second and third process data sets each include one or more process profiles and/or process responses, determining a first correlation between the first process data set and the second process data set, and determining a second correlation between the first process data and the third process data, and reconstructing a fourth process data set related to a performance of the second strain in the second process for producing bio-ethanol at the second site by missing data imputation, wherein the fourth process data set is estimated based on the first correlation and the second correlation.

The system enables a prediction of a performance of a strain capable of fermentation of biomass in a process at a certain plant, based on the performance of said strain in the process at another plant and the performance of another strain in the process at both plants.

Advantageously, the system for predicting the performance of the strain capable of fermentation of biomass in a process at a certain plant can be used for performing yeast optimization.

According to an aspect, the invention provides for a computer program product configured to be run on a machine for predicting performance of strains in processes, the strains being capable of fermentation of biomass for production of at least bio-ethanol. the computer program product is configured to: receiving a first process data set related to a performance of a first strain in a first process for producing bio-ethanol at a first site, receiving a second process data set related to a performance of a second strain in the first process for producing bio-ethanol at the first site, receiving a third process data set related to a performance of the first strain in a second process for producing bio-ethanol at a second site, the second site being different from the first site, and wherein the first, second and third process data sets each include one or more process profiles and/or process responses, determining a first correlation between the first process data set and the second process data set, and determining a second correlation between the first process data and the third process data, and reconstructing a fourth process data set related to a performance of the second strain in the second process for producing bio-ethanol at the second site by missing data imputation, wherein the fourth process data set is estimated based on the first correlation and the second correlation.

Advantageously, the invention provides for a computer program that is able to predict the performance of a particular strain in a process at a certain plant on which no data is available for the particular strain.

Different regression models can be employed for performing the missing data prediction step. A multivariate regression model may provide accurate results, but other techniques may also be used such as a projection model plane technique, trimmed scores regression, joint-Y partial least squares regression, maximum likelihood principal component analysis, piecewise direct standardization, etc. It will be appreciated that many variants are possible. It is also possible to use multivariate regression models and/or hybrid models.

It will be appreciated that any of the aspects, features and options described in view of the method apply equally to the method and the described system and computer program product. It will also be clear that any one or more of the above aspects, features and options can be combined.

BRIEF DESCRIPTION OF THE DRAWINGS

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawings.

DETAILED DESCRIPTION OF A PREFERRED EMBODIMENT

Figure 1:
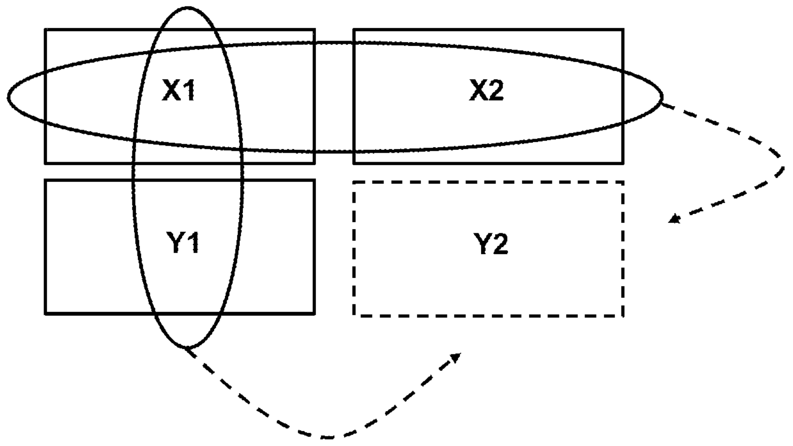
FIG. 1 shows a schematic diagram of an embodiment of a method for predicting performance of strains in processes.

FIG. 1 shows a schematic diagram of an embodiment of a method for predicting performance of a strain in a process. Values denoted by X represent process data sets related to a performance of a first strain, values denoted by Y represent process data sets related to a performance of a second strain. An index 1 in said values indicate that the process data set is related to a performance in a first process, an index 2 in said values indicate that the process data set is related to a performance in a second process.

X1 thus represents a first process data set related to a performance of a first strain in a first process for producing bio-ethanol at a first site, Y1 represents a second process data set related to a performance of a second strain in the first process for producing bio-ethanol at the first site, X2 represents a third process data set related to a performance of the first strain in a second process for producing bio-ethanol at a second site, the second site being different from the first site. The vertical oval, comprising X1 and Y1, represents a first correlation between the first process data set and the second process data set, the horizontal oval, comprising X1 and X2, represents a second correlation between the first process data and the third process data. Y2 represents a fourth, reconstructed, process data set related to a performance of the second strain in the second process for producing bio-ethanol at the second site by missing data imputation, wherein the fourth process data set is estimated based on the first correlation and the second correlation.

As used herein, "strains" are microbial strains, i.e. strains of a microorganism. In a preferred embodiment, the strains are bacterial or fungal strains, more preferably fungal strains and most preferably yeast strains. The "first strain" and the "second strain" are preferably different strains. In a preferred embodiment, the first strain and the second strain are from the same microorganism, preferably both fungi, more preferably both yeasts. Preferably, the first strain and the second strain are from the same genus, more preferably from the same species.

Examples of microorganisms used in bio-ethanol production include *Saccharomyces cerevisiae, Kluyveromyces marxianus, Pichia stipites, Issatchenkia orientalis* and *Zymomonas mobilis*, among others.

The performance of strains in processes can be predicted by means of a method including: receiving a first process data set X1 related to a performance of a first strain in a first process for producing bio-ethanol at a first site; receiving a second process data set Y1 related to a performance of a second strain in the first process for producing bio-ethanol at the first site;

receiving a third process data set X2 related to a performance of the first strain in a second process for producing bio-ethanol at a second site, the second site being different from the first site, and wherein the first, second and third process data sets X1, X2, Y1 each include one or more process profiles and/or process responses; determining a first correlation between the first process data set X1 and the second process data set Y1, and determining a second correlation between the first process data set X1 and the third process data set X2; and reconstructing a fourth process data set Y2 related to a performance of the second strain in the second process for producing bio-ethanol at the second site by missing data imputation, wherein the fourth process data set Y2 is estimated based on the first correlation and the second correlation.

The data sets may include a plurality of profiles in time, e.g. a consumption of sugar or a production of ethanol. Profiles of various other quantities can also be monitored and used. The profiles can be observed in function of time for each batch in each plant. The correlations between the measurements can be determined by means of comparing data of one plant versus data of another plant. This provides a first relationship correlating different plants for a particular strain, e.g. plant 1 and plant 2 for strain Y. Furthermore, another relationship can be determined by comparing data of one plant with a first strain and data of the same plant with another strain.

Figure 2:
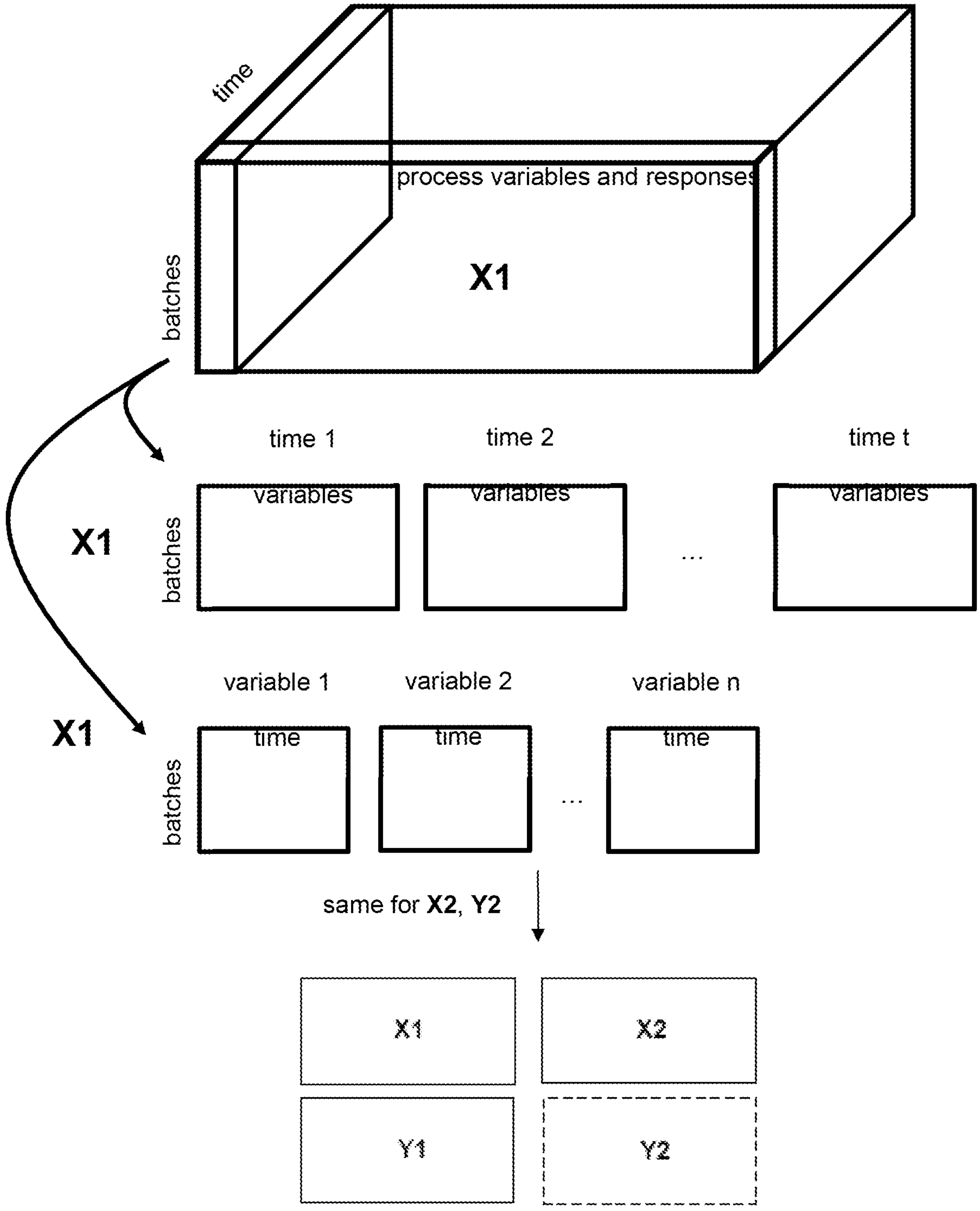
FIG. 2 shows a schematic diagram of an embodiment of input parameters and process data sets.

FIG. 2 shows a schematic diagram of an embodiment of input parameters and process data sets. Each process data set comprises multiple process parameters (process variables) and output parameters (responses), represented by rectangles behind each process data set. Multiple parameters can be visualized in a multidimensional grid, here depicted as a three-dimensional grid, wherein each axis represents a different parameter. Examples of parameters include pH, temperature, enzyme-concentration, feedstock composition, time, batch number, performance (measured in volume bio-ethanol per volume feedstock), $CO_2$-concentration. Missing data is solved by missing data imputation. Many missing data imputation methods exist, both single imputation and multiple imputation methods.

In an example, a first correlation between strain X and strain Y in a same plant is determined. Furthermore, a second correlation of strain Y in one plant and strain Y in a different plant is determined. These correlations can be used for predicting the performance of strain X in the second plant by means of missing data imputation. The technique can assume that a part of the data is missing and based on the above relationships/correlations, the missing part can be inferred. For instance, a regression model can be employed. However, as indicated above, a wide variety of models and techniques can be employed.

The data sets may be represented by matrices containing data (cf. profiles) collected at the first and second sites. X1 may correspond to data related to strain X in plant 1; X2 may correspond to data related to strain X in plant 2; Y1 may correspond to data related to strain Y in plant 1; and Y2 may correspond to data related to strain Y in plant 2. A correlation between X1 and X2, and a correlation between X1 and Y1 can be determined for predicting Y2 by means of missing data imputation.

A plurality of responses and profiles can be collected in function of time (t). The measurements may for instance be performed over a total duration of 48 hours with one measurement per hour (t=1:1:48). This can be done for a plurality of batches. The performance of the batches can be determined based on the profiles. The collected data can be represented in a 3D array. The collected 3D array can be unfolded in different ways, among them in a plurality of 2D arrays per time point or process variable.

Although in this example a 3D data set is retrieved, it is also possible to observe less parameters, obtaining a 2D data set. A combination of 2D and 3D data sets is also envisaged.

Data relating to strain X in plant 1 (cf. X1) can be unfolded, resulting in three data matrices concatenated batch-wise. This unfolding is analogous for strain X in plant 2 (cf. X2), and strain Y in plant 1 (cf. Y1). Matrices for strain Y in plant 1 (Y1), strain X in plant 1 (X1), and strain Y in plant 2 (Y2) can be used for determining a matrix for strain Y in plant 2 (Y2) via a missing data imputation algorithm (data of matrix block Y2 is missing). Based on correlations between columns of Y1 and Y2, and the relationships between Y1 and X1, a regression model can be used to predict the values in the missing block Y2. Similarly, X2 can be predicted if Y2 is already known.

Advantageously, the invention enables to predict how strain Y is going to perform and/or function in plant 2. It can be highly important to be able to accurately predict or estimate how the strain Y will perform in plant 2. For instance, plant 2 may be a new site necessitating the need to estimate or determine how a new strain is going to perform there. Based on this, better strains can be selected on new sites, or even process optimization can be performed.

Although many examples in the invention relate to bio-ethanol production processes, the invention is also applicable to other processes involving the use of strains for producing a product.

The data relating to batches for X1 and X2 may come from different sites (e.g. plants), making the only commonality the strain. Hence, a batch of one site may not correspond to a batch of another site. Optionally, data can be shuffled in X1 and/or X2. The shuffle can generate sufficient variation to better capture the differences. In this way, the accuracy of the prediction may be improved. The rows can be permuted in different ways, e.g. randomly.

Figure 3:
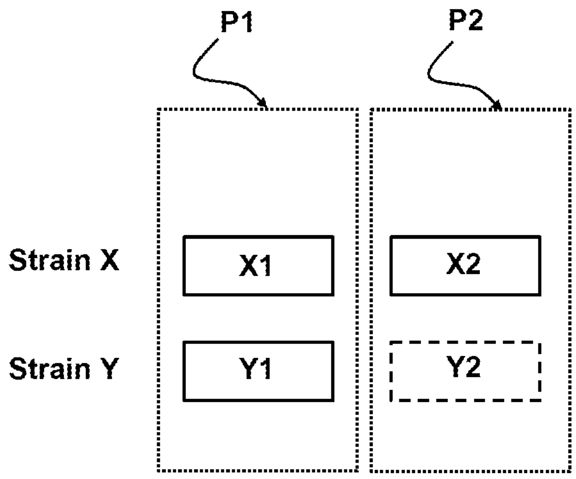
FIG. 3 shows a schematic diagram of an embodiment of a method wherein the first process at the first site is a laboratory environment, and wherein the second process at the second site is a plant.

FIG. 3 shows a schematic diagram of an embodiment of a method wherein the first process at the first site is a laboratory environment P1 (e.g. small-scale), and wherein the second process at the second site is a plant P2, for instance a large-scale industrial plant. A laboratory environment P1 comprises sites wherein only small volumes of bio-ethanol are being produced and are generally not intended for production and/or being sold. The laboratory environment P1 is preferably a biochemical laboratory environment, wherein yeast and/or other microbes can survive, e.g. due to the presence of an incubator. A plant P2 is preferably an industrial production plant, wherein large volumes of feedstock can be inserted, either in batch or in a continuous feed. Generally, the produced bio-ethanol is intended to be sold and is required to be of the same quality in each batch, or continuously of the same quality.

In some examples, existing strains may be adapted and/or improved or new strains may be made. The invention enables predicting how an (improved) strain may work at another site. For example, strain X can be a well-known strain that is currently used by some bio-ethanol producers in a P2 environment. From measured data of X and an improved strain Y in a P1 environment, it can be predicted how strain Y will perform at another site which can use a different process (process setting). It will be appreciated that different types of biomass may be used for bio-ethanol production. The biomass may for instance be corn. Different enzymes and/or pretreatments can be used in the process of producing the bio-ethanol.

Figure 4:
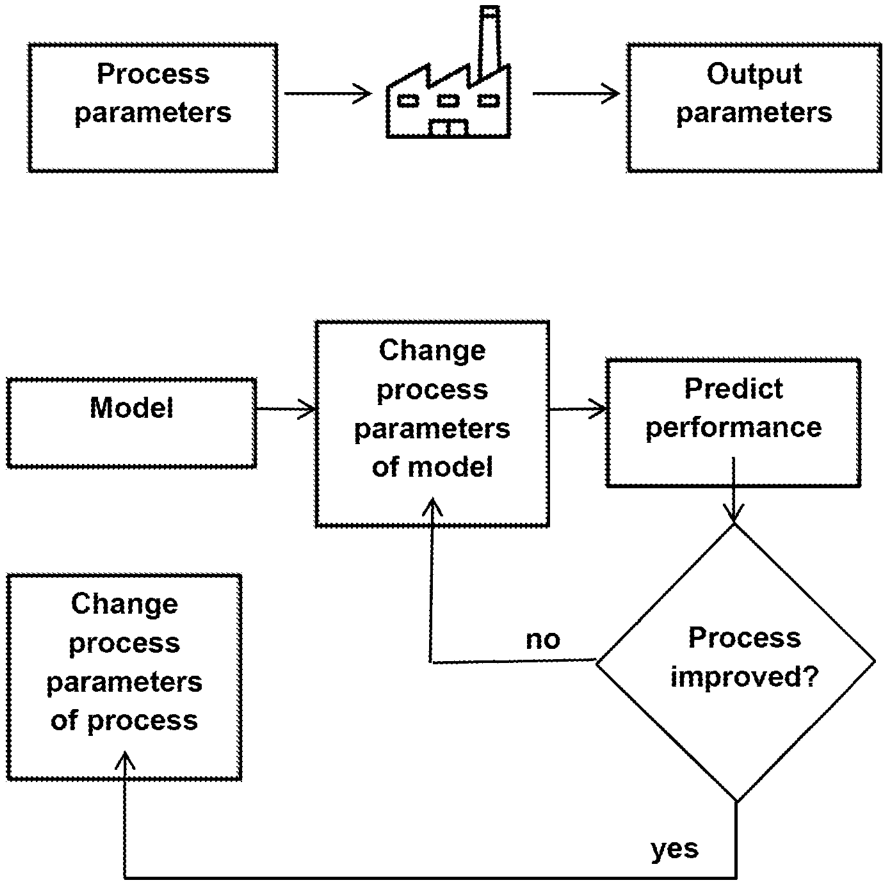
FIG. 4 shows a schematic diagram of an embodiment of a method wherein the reconstructed fourth process data set is used for fitting a predictive model configured to predict the performance of the second strain in the second process at the second site.

FIG. 4 shows a schematic diagram of an embodiment of a method wherein the reconstructed fourth process data set is used for fitting a predictive model configured to predict the performance of the second strain in the second process at the second site. In the upper diagram, it is schematically shown that process parameters are inputted into the site, which is preferably at least one of a laboratory environment or an industrial production plant.

The lower diagram shows a schematic representation of the decisions that are taken to optimize the production process of the second strain in the second process. A model is chosen for each of the process data sets. Many computational models exist that could be adequate. The missing data can be modelled by at least one of a regression model, which can optionally include multivariate regression, principal component regression, partial least squares regression, or trimmed scores regression for missing data imputation.

After modeling, process parameters are modified in the model and output parameters are simulated, resulting in a prediction of the performance. If the performance of the process has been improved, compared to before modification of the process parameters, the process parameters of the process itself can be modified in the same way in order to improve the process. If the process has not been improved, the process parameters of the model can be changed again and the decision process starts anew. The changing of the process parameters can be performed randomly, but more preferred is via a design of experiments. Various optimization algorithms can be employed.

Figure 5:
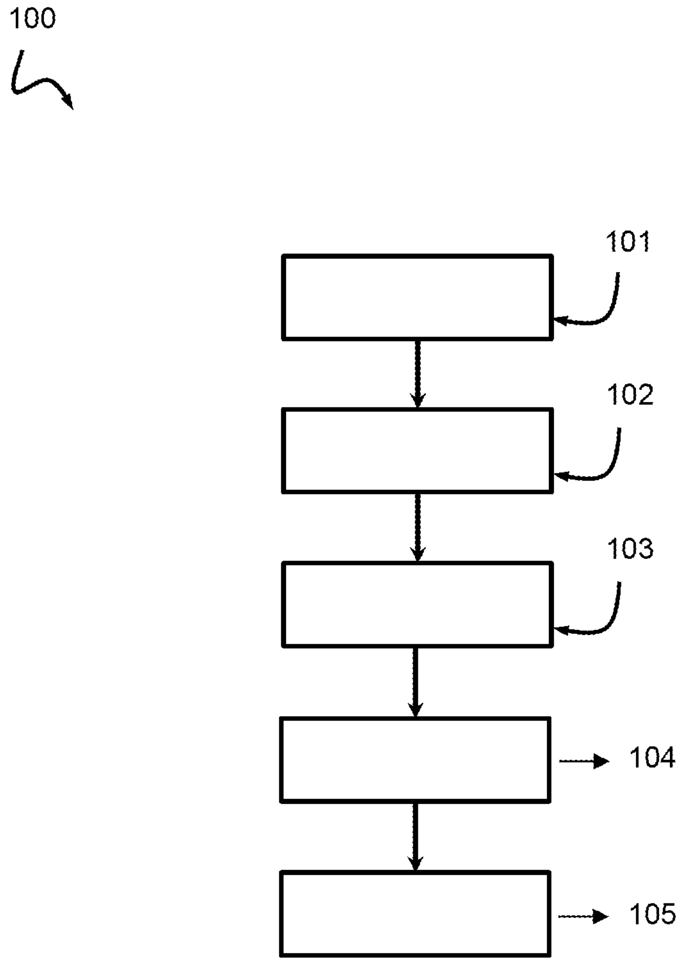
FIG. 5 shows a schematic diagram of a method.

FIG. 5 shows a schematic diagram of a method 100 for predicting performance of strains in processes. In some examples, the method is a computer implemented method configured to be run on a machine. In a first step 101, a first process data set is received related to a performance of a first strain in a first process for producing bio-ethanol at a first site. In a second step 102, a second process data set is received related to a performance of a second strain in the first process for producing bio-ethanol at the first site. In a third step 103, a third process data set is received related to a performance of the first strain in a second process for producing bio-ethanol at a second site, the second site being different from the first site, and wherein the first, second and third process data sets each include one or more process profiles and/or process responses. In a fourth step 104, a first correlation between the first process data set and the second process data set, and a second correlation between the first process data and the third process data, are determined. In a fifth step 105, a fourth process data set is reconstructed related to a performance of the second strain in the second process for producing bio-ethanol at the second site by missing data imputation, wherein the fourth process data set is estimated based on the first correlation and the second correlation.

It will be appreciated that the method may include computer implemented steps. All above mentioned steps can be computer implemented steps. Embodiments may comprise computer apparatus, wherein processes performed in computer apparatus. The invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program. For example, the carrier may comprise a storage medium, such as a ROM, for example a semiconductor ROM or hard disk. Further, the carrier may be a transmissible carrier such as an electrical or optical signal which may be conveyed via electrical or optical cable or by radio or other means, e.g. via the internet or cloud.

Some embodiments may be implemented, for example, using a machine or tangible computer-readable medium or article which may store an instruction or a set of instructions that, if executed by a machine, may cause the machine to perform a method and/or operations in accordance with the embodiments.

Various embodiments may be implemented using hardware elements, software elements, or a combination of both. Examples of hardware elements may include processors, microprocessors, circuits, application specific integrated circuits (ASIC), programmable logic devices (PLD), digital signal processors (DSP), field programmable gate array (FPGA), logic gates, registers, semiconductor device, microchips, chip sets, et cetera. Examples of software may include software components, programs, applications, computer programs, application programs, system programs, machine programs, operating system software, mobile apps, middleware, firmware, software modules, routines, subroutines, functions, computer implemented methods, procedures, software interfaces, application program interfaces (API), methods, instruction sets, computing code, computer code, et cetera.

Herein, the invention is described with reference to specific examples of embodiments of the invention. It will, however, be evident that various modifications, variations, alternatives and changes may be made therein, without departing from the essence of the invention. For the purpose of clarity and a concise description features are described herein as part of the same or separate embodiments, however, alternative embodiments having combinations of all or some of the features described in these separate embodiments are also envisaged and understood to fall within the framework of the invention as outlined by the claims. The specifications, figures and examples are, accordingly, to be regarded in an illustrative sense rather than in a restrictive sense. The invention is intended to embrace all alternatives, modifications and variations which fall within the spirit and scope of the appended claims. Further, many of the elements that are described are functional entities that may be implemented as discrete or distributed components or in conjunction with other components, in any suitable combination and location.

In the claims, any reference signs placed between parentheses shall not be construed as limiting the claim. The word ‘comprising’ does not exclude the presence of other features or steps than those listed in a claim. Furthermore, the words ‘a’ and ‘an’ shall not be construed as limited to ‘only one’, but instead are used to mean ‘at least one’, and do not exclude a plurality. The mere fact that certain measures are recited in mutually different claims does not indicate that a combination of these measures cannot be used to an advantage.

The invention claimed is:

1. A computer-implemented method for predicting performance of one or more strains in one or more batch processes, the strains being capable of fermentation of biomass for production of at least bio-ethanol, the method comprising:

receiving a first process data set related to a performance of a first strain in a first batch process for producing bio-ethanol at a first site, receiving a second process data set related to a performance of a second strain in the first batch process for producing bio-ethanol at the first site, receiving a third process data set related to a performance of the first strain in a second batch process for producing bio-ethanol at a second site, the second site being different from the first site, and wherein the first, second and third process data sets each include one or more process profiles and/or process responses, determining a first correlation between the first process data set and the second process data set, and determining a second correlation between the first process data set and the third process data set, reconstructing a fourth process data set related to a performance of the second strain in the second batch process for producing bio-ethanol at the second site by missing data imputation, wherein the fourth process data set is estimated based on the first correlation and the second correlation, and using the reconstructed fourth process data set to produce bio-ethanol using the second strain in the second batch process at the second site;

wherein:

the first batch process at the first site and the second batch process at the second site are carried out at remote locations with respect to each other;

the first site and the second site have different process settings; and the fourth process data set comprises a new unmeasured data set for the second strain at the second site, wherein the second strain has not been tested in the second batch process at the second site prior to the reconstructing.

2. The method according to claim 1, wherein the reconstructed fourth process data set is used for fitting a predictive model configured to predict the performance of the second strain in the second batch process at the second site.

3. The method according to claim 2, wherein a predictive model is employed for adjusting operational parameters in order to improve the performance of the second strain in the second batch process at the second site.

4. The method according to claim 1, wherein the first batch process at the first site is carried out in a laboratory, and wherein the second batch process at the second site is carried out in a plant, the plant optionally being an industrial-scale bio-ethanol production plant.

5. The method according to claim 4, wherein one or more small-scale laboratory experiments are carried out in the laboratory for determining at least one of the first process data set or the second process data set.

6. The method according to claim 1, wherein the first batch process at the first site is modelled by means of a computational model, wherein the computational model is used for determining at least one of the first process data set or the second process data set.

7. The method according to claim 1, wherein missing data related to the performance of the second strain in the second batch process at the second site is predicted at least in part using a regression model.

8. The method according to claim 7, wherein the regression model includes at least one of: multivariate regression, principal component regression, partial least squares regression, or trimmed scores regression for missing data imputation.

9. The method according to claim 1, wherein prior to determining the second correlation, data arrays in the data set relating to different batches in the first process data and the third process data are shuffled with respect to each other.

10. The method according to claim 9, wherein the data arrays are shuffled randomly or pseudo-randomly.

11. The method according to claim 1, wherein missing data related to the performance of the second strain in the second batch process at the second site is predicted at least in part using a trained artificial neural network model.

12. The method according to claim 1, wherein the first batch process at the first site and the second batch process at the second site are carried out in industrial-scale bio-ethanol production plants different from each other.

13. The method according to claim 1, wherein the process data sets include for a plurality of time points a value indicative for at least one of a sugar consumption, ethanol production, pH value, reaction temperature, composition of biomass, enzyme composition, yeast cell count, or glycerol production.

14. A system for predicting performance of one or more strains in one or more processes, the system including computational means for carrying out the method according to claim 1.

15. The method according to claim 1, wherein the different process settings comprise different quantities of an ingredient used in the first batch process and the second batch process.

16. The method according to claim 2, wherein the predictive model further receives additional data relating to a recipe used in the second batch process at the second site.

17. The method according to claim 1, wherein the reconstructed fourth process data set includes a process response, and wherein a design of experiments response model is used to predict an optimized parameter set for the second batch process at the second site.

18. The method according to claim 1, wherein the second strain is an improvement of the first strain.

* * * * *